United States Patent [19]

Lamminkari et al.

[11] 4,153,622

[45] May 8, 1979

[54] PROCESS FOR THE RECOVERY OF β-SITOSTEROL

[75] Inventors: Eero K. Lamminkari; Lasse A. Koskenniska, both of Oulu, Finland

[73] Assignee: Medipolar Oy, Oulu, Finland

[21] Appl. No.: 907,182

[22] Filed: May 18, 1978

[51] Int. Cl.² ............................................. C07J 9/00
[52] U.S. Cl. ............................................. 260/397.25
[58] Field of Search ................................. 260/397.25

[56] References Cited

U.S. PATENT DOCUMENTS 3,332,969  7/1967  Hutt Jr. .......................... 260/397.25
4,044,031  8/1977  Johansson et al. ............... 260/397.25

*Primary Examiner*—Elbert L. Roberts
*Attorney, Agent, or Firm*—J. Harold Nissen

[57] ABSTRACT

A process for the isolation of technical grade β-sitosterol from the mixture of sterols in unsaponifiables obtained from crude soap skimmings. The unsaponifiables, usually called the neutral fraction, are dissolved in acetone, filtrated with active carbon, the acetone filtrate is concentrated, ethanol is added and, after cooling, the precipitated β-sitosterol is centrifuged or filtered from the mixture.

13 Claims, 1 Drawing Figure

PROCESS FOR THE RECOVERY OF β-SITOSTEROL

BACKGROUND OF THE INVENTION

The steroids in general form an important group of the modern drugs. An important one of these, β-sitosterol, is both a lipotropic agent and a starting material in the production of steroids.

The technical grade β-sitosterol obtained according to this invention is pure enough for the use as starting material for steroids and is also in a form which is easily purifiable by conventional methods to pharmaceutical grade β-sitosterol.

Many processes for the separation of sterols from various sources are known but there are not many processes which concern particularly the separation of β-sitosterol from the neutral fraction obtained in the sulfate process of pine wood and hardwood. The U.S. Pat. No. 2,835,682 for example concerns the recovery of sterols from sterol-containing materials in general. According to this patent a sterol containing mixture is fractioned in a normally gaseous hydrocarbon, e.g. propane, to give a sterol-enriched fraction, which is saponified in alcholic alkali solution whereafter the sterols are crystallized by adding water and cooling. U.S. Pat. No. 2,866,797 is concerned with the crystallization of sterols from unsaponifiables obtained from vegetable oils, tall oils, sugar cane oil and the like. The unsaponifiable fraction is extracted with ethylene dichloride, and small amounts of water and methanol are added to precipitate the sterols.

Of newer publications can be mentioned U.S. Pat. No. 3,961,211, which concerns a process for preparing sterols from plant sources, especially tall oil pitch, by extraction in a water-alcohol-hydrocarbon mixture followed by saponification and subsequent recrystallization and leaching. The process, which is not comparable to the process of the invention as the starting material is different, gives a good yield of a mixture containing β-sitosterol and campesterol.

In Chemical Abstracts, Vol. 81 (1974) 51409 v a method is described for purifying crude phytosterol derived from sulfate soap to β-sitosterol. The process comprises dissolving in ligroin at 70°-75° C., extracting with 40 percent ethanolic solution at 65°-70° C., and washing with water at 65°-70° C. The solution is then cooled to give 90.4 percent pure β-sitosterol, the yield being 69.5 percent.

U.S. Pat. No. 4,044,031 disclosed a process for the separation of sterols from e.g. the same neutral fraction as in the present invention. The process of U.S. Pat. No. 4,044,031 consists of dissolving the neutral fraction in a water-immiscible solvent, extracting the solution with a hydrophilic phase containing small amounts of water, and recovering sterols from the hydrophilic phase. This process, which utilizes extraction with two solvent phases, can be carried out continuously utilizing a counter-current extraction process.

As compared with all above mentioned processes the process of the present invention is inexpensive and simple and gives a product of high quality. The betulin, which usually accompanies the β-sitosterol in the purification processes and which is a toxic agent, is completely removed in the process of the present invention.

BRIEF DESCRIPTION

The present invention relates to an improved process for the isolation of β-sitosterol from the unsaponifiable neutral substances obtained according to the process described in U.S. Pat. No. 3,965,085. The invention more specifically concerns a simple and economical process for the isolation of β-sitosterol, in a purity of about technical grade, from the unsaponifiable neutral substances, hereafter called the neutral fraction, obtained as a byproduct of soap manufacturing from the crude soap skimmings of the sulfate pulp process using as raw material both pine wood and hardwood, especially birch.

The neutral fraction usually contains over 10 percent of β-sitosterol. In addition betulin, betulaprenols, α-sitosterol, campesterol and other neutral substances such as squalene, lignoseryl alcohol and behenyl alcohol and other similar constituents are normally present.

According to the present invention a process on an industrial scale has been developed, by which technical grade β-sitosterol is isolated from the neutral fraction which contains 70-80 percent of β-sitosterol, the total content of sterols being about 95 percent.

DESCRIPTION OF THE PREFERRED EMBODIMENT

Figure 1:
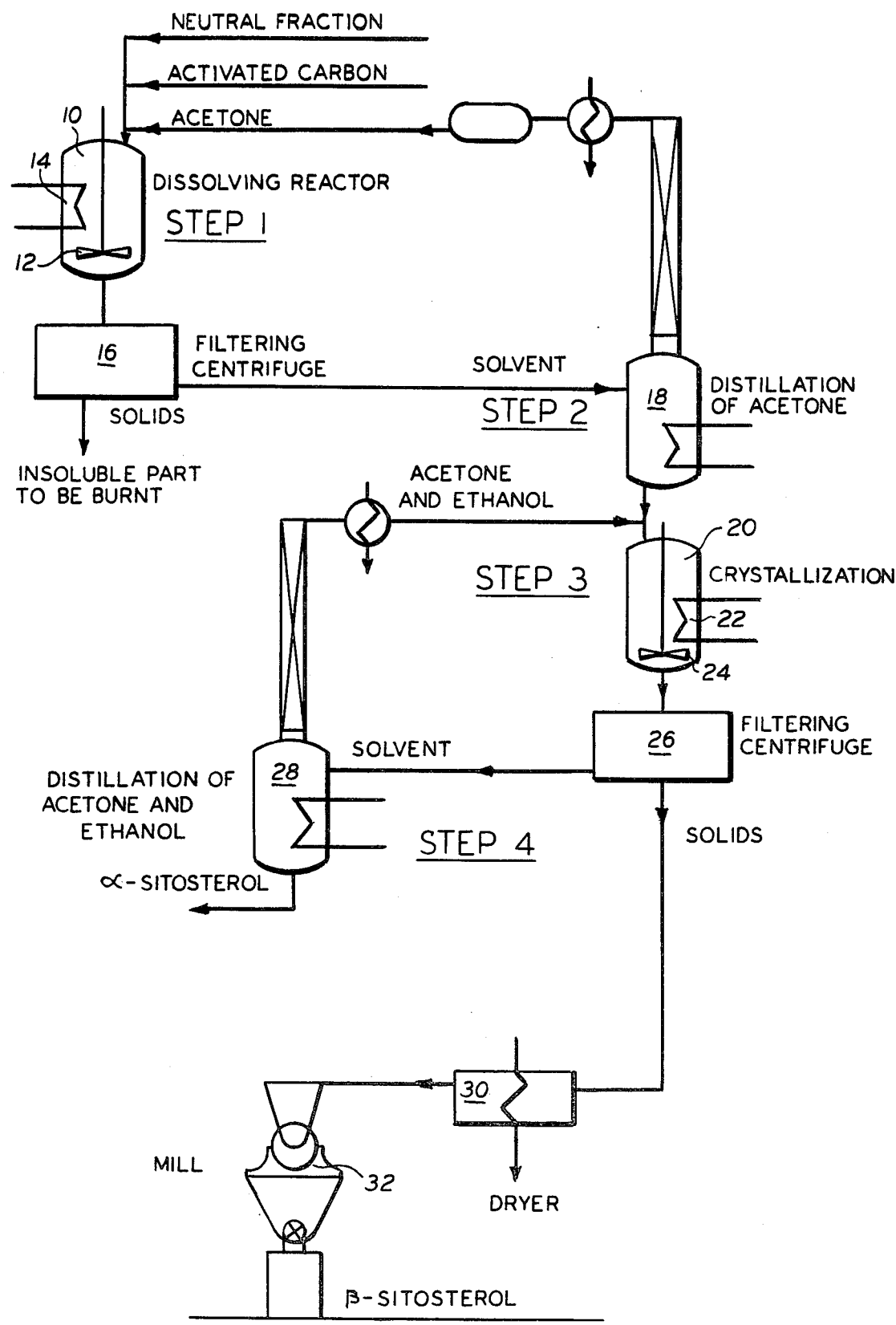
FIG. 1 shows a schematic flow diagram for a continuous operation utilizing the present invention process.

With reference to FIG. 1, the preferred embodiment can be described in a number of steps or stages.

Step 1. In general, the present invention comprises suspending the neutral fraction and activated carbon in acetone at a temperature from about 40° C. to about the point at which acetone begins to boil off, preferably in the range of 40°-50° C., and preferably in a reaction vessel 10 equipped with agitation 12 and heating devices 14. The ratio of neutral fraction to acetone is preferably in the range of 1:3 to 1:10 and the ratio by weight of carbon to neutral fraction is preferably in the range of 1:20 to 1:60. The insoluble part and the carbon are separated, for example by filtering in a cetrifuge device 16, whereby most of the impurities are removed in the solid part, namely the betula prenols, betulin, sitostanol, squalene, lignoseryl alcohol and behenyl alcohol. In this procedure also the color and odor are removed almost completely.

The β-sitosterol remaining in solution includes as impurities mainly only campesterol and α-sitosterol. These impurities are partly removed by selectively precipitating the β-sitosterol from a solvent mixture as described in the following steps.

Step 2. For this step, the main part of the acetone is distilled off from the filtrate utilizing usual distillation apparatus 18. The acetone is preferably almost completely distilled off and recycled as shown in FIG. 1. After this the residue is redissolved in a mixture of acetone and alcohol, preferably ethanol. Proportions of acetone to ethanol ranging from about 4:1 to 1:2 have been found to give good results. The preferred proportion by volume is 5:2, whereby a product containing over 70 percent of β-sitosterol is obtained in good yield.

Of other alcohols which are usable can be mentioned methanol and isopropanol. β-sitosterol is less soluble in acetone-methanol than in acetone-ethanol, and more soluble in acetone-isopropanol than in either mixture.

Thus, when isopropanol is used, the proportion of acetone to isopropanol is preferably in the range of 5:1 to 5:2. With methanol, the preferred acetone to methanol proportion is in the range of 5:1 to 1:2.

Step 3. The β-sitosterol fraction can be recovered by cooling the acetone-ethanol solution sufficiently to cause it to precipitate from solution. This is preferably accomplished utilizing crystallizing apparatus 20 normally having temperature control 22 and agitating devices 24. Most of the impurities remain in solution.

Step 4. The precipitate is separated in a filtering device 26 and dried. The solvent is preferably recovered in a distillation type of device 28 for reuse. β-sitosterol precipitates in crystalline form and is dried in drier 30.

Although precipitation or cyrstallization may be carried out over a wide range of temperatures spanning at least 20° C. to −10° C., it is advantageously carried out in a temperature range of about −5° C. to +5° C. whereby good yields are obtained. The main part of the α-sitosterol remains in the mother liquor and is recoverable from the distillation apparatus 28.

The resulting crystalline β-sitosterol may be prepared as required for further use by milling 32 or other processes not part of this invention.

The process of the invention can be performed as a batch operation although a continuous process such as shown in FIG. 1 is best for economical reasons. In the batch operation it is preferable to distil off part of the acetone. The removing of acetone permits a reduction in the amount of alcohol which needs to be added but this is not necessary for the process to operate.

In the described process technical grade β-sitosterol, with a β-sitosterol content of about 75 percent and a total sterol content of about 95 percent, is recovered with relatively small costs for raw materials and labor. In the process nearly all compounds which would disturb the further processing to steroid precursors are removed. In this way about 70 percent of the β-sitosterol present in the neutral fraction can be recovered.

In the process the quality of the product can be improved by increasing the proportion of ethanol in the crystallization procedure. The obtained technical grade β-sitosterol can be recrystallized with known methods and used as a pharmaceutical raw material. From the mother liquor of the crystallization α-sitosterol in comparatively pure form can be isolated.

In the following the invention is described by examples, two of which are comparative examples which show, that the processes of U.S. Pat. No. 3,691,211 and C.A. 81 (1974) 51409 v are inferior to the process of the invention when using the neutral fraction as starting material. The neutral fraction used in all examples contains 12.5 percent of β-sitosterol, about 25 percent of betula prenols, 10 percent of α-sitosterol, 7 percent of campesterol and 10 percent of betulin.

EXAMPLE 1 (batch operation)

200 kg of neutral fraction and 5 kg of activated carbon are suspended in 1,000 liters of acetone and the temperature of the mixture is raised to 40°–50° C. The mixture is filtered on a pressure filter. From the filtrate 500 liters of acetone is distilled off and 200 liters of ethanol is added. The solution is heated to about 50° C. and cooled to 0°–5° C. and the obtained β-sitosterol fraction is separated. The yield of colorless crystals after drying is 23.5 kg. A gas chromatographic analysis of the product gives the following result: 72.2 percent of β-sitosterol, 6.1 percent of campesterol and 16.8 percent of α-sitosterol. The total content of sterols is thus 94 percent and the product is free from betulin.

EXAMPLE 2

200 kg of the neutral fraction is treated as in example 1 with the difference that the proportion of acetone and ethanol by volume is 1:1. The yield is 20 kg of white crystals. A gas chromatographic analysis shows that the content of β-sitosterol is 80.8 percent, the content of campesterol is 6.1 percent and the content of α-sitosterol is 11.7 percent, giving a total sterol content of 98.6 percent. The product is betulin-free.

EXAMPLE 3

200 kg of the neutral fraction is treated as in example 1 but the proportion of acetone and ethanol by volume is 1:2. The yield of white crystals is 15 kg. A gas chromatogram gives a β-sitosterol content of 84 percent, a campesterol content of 4 percent, a α-sitosterol content of 12 percent and no betulin. The total sterol content is thus 100 percent.

EXAMPLE 4

200 kg of the neutral fraction is treated as in example 1, but the proportion of acetone and ethanol by volume is 3:1. The yield is 25 kg of white crystals, with a β-sitosterol content of 70.0 percent, a campesterol content of 8.5 percent and α-sitosterol content of 18.2 percent.

EXAMPLE 5

2 kg of the neutral fraction is suspended in 8 liters of acetone. 32 g of activated carbon is added and the temperature of the mixture is raised to 40°–50° C. The mixture is filtered and 2 l of ethanol is added to the filtrate. The solution is cooled to 0° C. and the precipitate is separated by filtration. The yield is 200 g of colorless product which contains 68.5 percent of β-sitosterol, 7.0 percent of campesterol and 23.5 percent of α-sitosterol.

EXAMPLE 6 (comparative example)

2 kg of the neutral fraction are treated as in U.S. Pat. No. 3,696,211, example 1, step D. The substance is thus refluxed in the 10 liters of methyl ethyl ketone for 45 minutes and centrifuged hot. The methyl ethyl ketone is distilled off and the residue is refluxed in 3 liters of methanol for 1 hour, filtered at 60° C. and washed with cold methanol and dried. The yield of brown product is 200 g. A gas chromatogram of the product shows that the content of β-sitosterol is 55.9 percent, the content of campesterol is 15 percent and the content of α-sitosterol is 25 percent.

EXAMPLE 7 (comparative example)

2 kg of the neutral fraction is treated as in the process of C.A. 81 (1974) 51409v. It is thus dissolved in 10 liters of ligroin at 75° C. and the solution is washed with 10 liters of 40 percent ethanol at 65° C. and then with water at 65° C. The ligroin solution is then cooled at 13° C., whereby the obtained product is so pasty that it is quite impossible to handle.

EXAMPLE 8

2 kg of the neutral fraction is suspended in 8 liters of acetone. 32 g of activated carbon is added and the temperature of the mixture is raised to 40°–50° C. The mixture is filtered and 1.6 l of isopropanol is added to the filtrate. The solution is cooled to −5° C. and the precipitate is separated by filtration. The yield is 160 g of colorless product which contains 68.3 percent of β-sitosterol, 10.7 percent of campesterol and 20.9 percent of α-sitosterol.

EXAMPLE 9

2 kg of the neutral substance is treated as in Example 8, and after the first filtration 3.2 liters of isopropanol is added, and the solution is cooled to 0° C. The yield of 80 g of a product containing 73.6 percent of β-sitosterol, 8.5 percent of campesterol and 17.9 percent of α-sitosterol.

EXAMPLE 10

2 kg of the neutral substance is treated as in Example 8 but in place of isopropanol is added 1.6 liters of methanol and the solution is cooled to 0° C. The yield of colorless crystals is 192 g containing 60.1 percent of β-sitosterol, 9.9 percent of campesterol and 30.0 percent of α-sitosterol.

EXAMPLE 11

2 kg of neutral substance is treated as in the foregoing example, but the quantity of methanol is 4.8 liters. The yield is 256 g, the β-sitosterol content is 59.9 percent, the α-sitosterol content is 30.1 percent and the campesterol content is 10.1 percent.

EXAMPLE 12

2 kg of the neutral substance is treated as in Example 7, but the quantity of methanol is 16 liters. The yield is 256 g, the β-sitosterol content 59.2 percent, the α-sitosterol content 30.6 percent and the campesterol content 9.8 percent.

EXAMPLE 13 (continuous process)

The process is described by the following scheme:

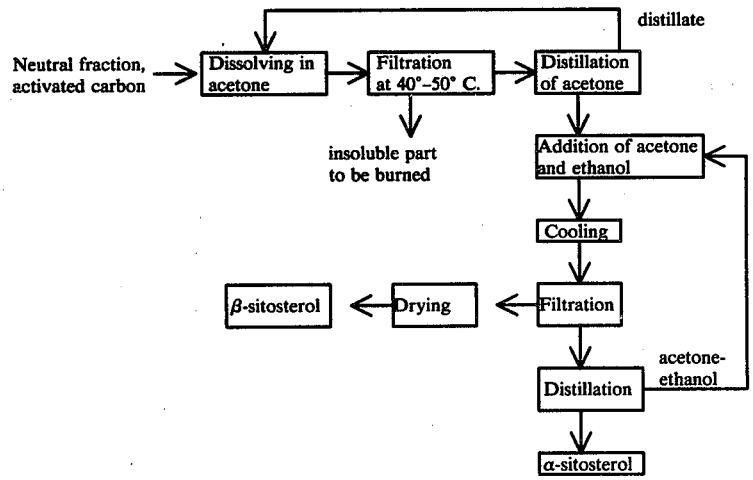

What is claimed is:

1. A process for recovery of β-sitosterol from the unsaponifiable or "neutral" fraction resulting from the manufacturing of soap by the sulfate pulp process, comprising the steps of:
   a. suspending the neutral fraction together with activated carbon in acetone
   b. raising the suspension temperature into the range of from about 40° C. to about the boiling-off point of the acetone in the mixture whereby a portion of the neutral fraction forms a solution with the acetone; thereafter
   c. separating the solution from the insoluble part and the carbon; subsequently
   d. adding ethanol to the solution to produce a ratio by volume of acetone: ethanol of 4:1 to 1:2
   e. adjusting the temperature of the solution to be in the range of about 50° C. to the boiling point of the solution; and thereafter
   f. cooling the solution thereby to separate out β-sitosterol from the solution.

2. A process as claimed in claim 1, further including the step of distilling off part of the acetone before adding the ethanol.

3. A process as claimed in claim 1 wherein the suspension (step b) is raised to a temperature of about 40° C. to about 50° C.

4. A process as claimed in claim 3 wherein the solution is cooled (step 1. f) to a range of about −5° C. to about 5° C.

5. A process as claimed in claim 4 wherein the ratio of acetone to ethanol (step 1. d) is about 5:2.

6. A process for recovery of β-sitosterol from the unsaponifiable or "neutral" fraction resulting from the manufacturing of soap by the sulfate pulp process, comprising the steps:
   a. suspending the neutral fraction along with activated carbon in acetone;
   b. raising the suspension temperature into the range of from about 40° C. to about the boiling-off point of the acetone in the mixture whereby a portion of the neutral fraction forms a solution with the acetone; thereafter
   c. separating the insoluble part and the carbon from the solution; subsequently
   d. substantially removing all of the solvent from the solution separated from the suspension, leaving a residue;
   e. redissolving the residue in a mixture of acetone and ethanol in the ratio by volume of about 4:1 to about 1:2; thereafter
   f. adjusting the temperature of the solution to be in the range of about 50° C. to the boiling point of the solution; and thereafter
   g. cooling the solution thereby to separate out β-sitosterol from the solution.

7. A process as claimed in claim 6 wherein the suspension (step b) is raised to a temperature of about 40° C. to about 50° C.

8. A process as claimed in claim 7 wherein the solution is cooled (step 6. g) to a range of about −5° C. to about 5° C.

9. A process as claimed in claim 8 wherein the ratio of acetone to ethanol (step 6. e) is about 5:2.

10. A process as claimed in claim 9 wherein the cooled solution (step 6. g) is centrifuged to aid in recovery of the β-sitosterol.

11. A process as claimed in claim 10 wherein the solvent is substantially all removed (step 6. d) by a distillation process which recovers the solvent.

12. A process as claimed in claim 5 wherein the cooled solution (step 1. f) is filtered to remove the β-sitosterol.

13. A process for recovery of β-sitosterol from the unsaponifiable or "neutral" fraction resulting from the manufacturing of soap by the sulfate pulp process, comprising the steps of:
 a. suspending the neutral fraction together with activated carbon in acetone;
 b. raising the suspension temperature into the range of from about 40° C. to about the boiling-off point of the acetone in the mixture whereby a portion of the neutral fraction forms a solution with the acetone; thereafter
 c. separating the solution from the insoluble part and the carbon; and subsequently
 d. selectively precipitating the β-sitosterol from said portion of solution by establishing an acetone-alcohol mixture as the solvent for the solution, wherein the alcohol is methanol, ethanol, propanol or a mixture thereof; and
 e. cooling the resulting solution to separate out the β-sitosterol.

* * * * *